United States Patent [19]

Kanno et al.

[11] Patent Number: 4,770,046

[45] Date of Patent: Sep. 13, 1988

[54] METHOD OF AND SYSTEM FOR ASSESSING THE SAFETY OF SHRINKAGE FITTED TYPE ROTOR

[75] Inventors: Satoshi Kanno, Hitachi; Shinji Sakata, Katsuta; Tasuku Shimizu, Hitachi; Ryoichi Kaneko, Hitachi; Kiyoshi Shimomura, Hitachi; Naoaki Shibashita, Hitachi, all of Japan

[73] Assignee: Hitachi, Ltd., Tokyo, Japan

[21] Appl. No.: 922,291

[22] Filed: Oct. 23, 1986

[30] Foreign Application Priority Data

Oct. 23, 1985 [JP] Japan ................................. 60-235177

[51] Int. Cl.$^4$ ............................................. G01N 22/02
[52] U.S. Cl. ......................................... 73/799; 73/572
[58] Field of Search ................... 73/799, 572; 364/508

[56] References Cited

U.S. PATENT DOCUMENTS 4,408,294 10/1983 Imam .................................... 364/508
4,635,210 1/1987 Shiohata et al. ..................... 364/508

OTHER PUBLICATIONS

Paris, P. C. et al., The Theory of . . . Crack Growth, ASTM STP 668, 1979, pp. 5-36.

*Primary Examiner*—Jerry W. Myracle
*Attorney, Agent, or Firm*—Antonelli, Terry & Wands

[57] ABSTRACT

A method system for assessing the safety of a rotor of a shrinkage fitted type wherein an opening displacement of a crack is determined an elastic-plastic fracture method and a reduction in shrinkage fitting force is calculated based on the crack opening displacement. The safety of the rotor is assessed based on the reduction in shrinkage fitting force caused to occur by the opening of the crack.

7 Claims, 6 Drawing Sheets

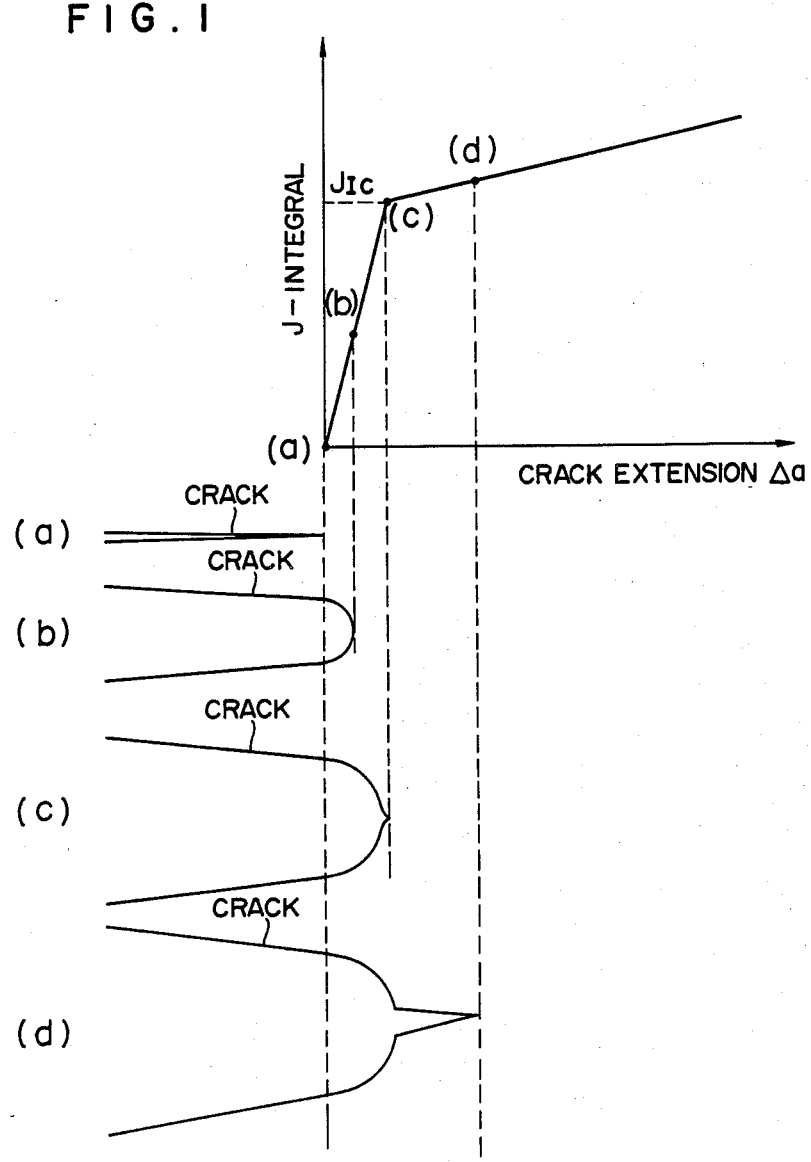

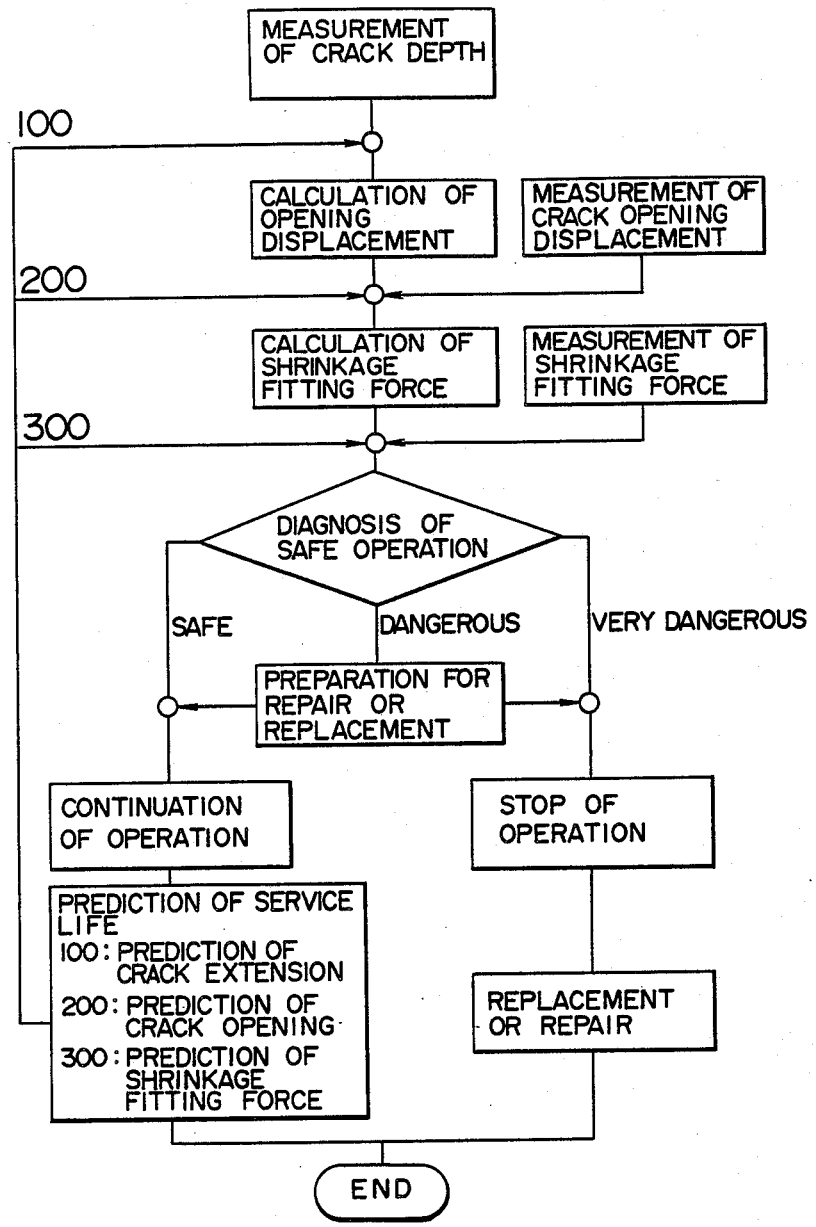

METHOD OF AND SYSTEM FOR ASSESSING THE SAFETY OF SHRINKAGE FITTED TYPE ROTOR

BACKGROUND OF THE INVENTION

This invention relates to a method and system for assessing the safety of rotors of a shrinkage fitted type, and, more particularly, to a method and system for assessing the safety of a rotor of a shrinkage fitted type, which is suitable for preventing the occurrence of accidents which might otherwise be caused by a reduction in shrinkage fitting force or power.

Heretofore, it has been usual practice to rely, for assessing the safety of rotors of a shrinkage fitted type, on a method which uses a stress intensity factor K based on the techniques of the elastic fracture mechanics. It is well known that the basic concept for this method is that fracture occurs when the stress intensity factor K reaches the material's constant $K_{IC}$. However, materials have in recent years been developed with an eye to increasing their toughness, and this has made it impossible to neglect the phenomenon of plastic deformation occurring at a crack tip. Thus, there has been a tendency to doubt the usefulness of the method of assessing safety based on the elastic fracture mechanics which neglects the plastic deformation. As a result, a method of assessing safety based on the concept of J-integral in the elastic-plastic fracture mechanics has in recent years been used in place of the method of assessing safety based on the techniques of the elastic fracture mechanics. As described in "The Theory of Instability of the Tearing Mode of Elastic-Plastic Crack Growth" by P. C. Paris et al., this method is based on the concept that fracture occurs in a structure of high toughness when the J-integral around a crack tip reaches the materials's constant $J_{IC}$ (the elastic-plastic fracture toughness). The deformation behavior of a crack is such that the crack tip opens before fracture commences and considerable opening takes place in the entire crack. The higher the toughness of material, the more marked is the opening deformation behavior of a crack. Thus, with the tendency of increasing the toughness of materials in recent years, the opening deformation of a crack has raised a new problem. In a rotor of a shrinkage fitted type, for example, when a crack is formed at the disc fitting portion of a fitted member which is shrinkage fitted over a rotary shaft, shrinkage fitting force would be reduced by the opening of the crack before fracture of the fitted member occurs, with the result that there is play between the rotary shaft and fitted member. When this happens, the fitted member would vibrate and cause damage to stationary members (casing, stator blades, etc.) by contacting them. In methods of the prior art for assessing the safety of the rotors (K, J-integral), assessment has been made based on fracture occurring as a sequel to the development of a crack inherent in a structure and the problem noted hereinabove has not been taken into consideration. Thus, to achieve a safe operation of a rotor of a shrinkage fitted type formed with a crack, it is necessary to pay attention to a reduction in shrinkage fitting force which would be caused to occur by the opening deformation of the crack. There has hitherto been no proposal made to assess the safety of rotors of a shrinkage fitted type from this point of view.

OBJECT AND SUMMARY OF THE INVENTION

This invention has as its object the provision of a method and system for assessing the safety of rotor of a shrinkage fitted type, intended to assess a reduction in shrinkage fitting force caused by the opening of a crack formed in the rotor to prevent the occurrence of play in a fitted member which might otherwise be caused by the reduction in shrinkage fitting force.

In a rotor of a shrinkage fitted type including a rotary shaft and a fitted member shrinkage fitted over the rotary shaft, it has been found that, in the event a crack is formed in the fitting portion of the fitted member, the opening deformation of the crack which occurs before fracture commences causes a reduction in shrinkage fitting force, with a result that trouble occurs in the operation of the rotor. The higher the toughness of material, the greater is the opening deformation of a crack before fracture commences. It would be considered that, in view of the tendency of materials becoming increasingly tougher in the future, attention should be paid to the problem that the opening deformation of a crack causes a reduction in shrinkage fitting force. Assume, for example, that the opening deformation of a crack has resulted in a total loss of shrinkage fitting force. The fitted member would become loose and vibrate, as a result, the fitted member would strike the stator and casing surrounding the fitted member, so that the operation of the rotor would become dangerous before fracture occurs in the fitted member.

Thus, to operate a rotor of a shrinkage fitted type having a crack without any risk, it would be necessary to assess not only the fracture of a fitted member but also a reduction in shrinkage fitting force caused by the opening deformation of a crack. Therefore, it is proposed in the invention to assess the safety of operation of the rotor based on a reduction in shrinkage fitting force caused by the opening deformation of a crack.

According to one aspect of the invention, there is provided a method of assessing the safety of a rotor of a shrinkage fitted type including a rotary shaft and a fitted member shrinkage fitted over the rotary shaft, the method comprising the steps of measuring a depth of a crack formed in a fitting portion of the fitted member; determining an opening in the crack by the techniques of the dynamics of elastic-plastic fracture mechanics; and calculating a reduction in shrinkage fitting force based on the opening displacement, to thereby assess the safety of the rotor.

According to another aspect of the invention, there is provided a system for assessing the safety of a rotor of a shrinkage fitted type including a rotary shaft and a fitted member shrinkage fitted over the rotary shaft, the system comprising a ultrasonic flaw detector for detecting a crack in the fitted member and generating a signal; a measuring and processing unit for determining a depth of the crack based on the signal from the flaw detector to generate an electric signal representative of the depth of the crack; and a computer for determining an opening displacement of the crack based on the electric signal from the measuring and processing unit to calculate a reduction in shrinkage fitting force based on the opening displacement, to thereby assess the safety of the rotor.

BRIEF DESCRIPTION OF THE DRAWINGS

FIG. 1 is a graphical representation of the opening deformation behavior of a crack in the method of assessing the safety of a rotor of a shrinkage fitted type according to the invention;

FIG. 4 is a flow chart showing the process steps of the method of assessing the safety of the rotor;

DETAILED DESCRIPTION

FIG. 1 is a diagrammatic representation of the deformation behavior of a crack based on the dynamics of elastic-plastic fracture mechanics and the relationship between the J-integral and the crack extension $\Delta a$. In FIG. 1, (a) designates a crack having a sharp tip formed in a fitted member prior to loading. Loading subjects the crack to tearing or opening deformation and causes blunting of the sharp tip as designated by (b). When the opening of the crack reaches a certain value ($J_{IC}$), crack extension commences at the blunted tip of the crack as indicated by (c), and the crack extension develops (d) until fracture of the fitted member occurs.

Thus, to increase the safety of the fitted member, one only has to use material of high elastic-plastic toughness $J_{IC}$. However, the higher the toughness of the material, the greater is the opening deformation of a crack before crack extension takes place at the blunted tip of the crack. Therefore, when the safety of a rotor of a shrinkage fitted type is considered, assessment should be made by taking into consideration the opening deformation of a crack to which no attention has ever been made, aside from the usual practice of determining whether rupture has taken place based on $J_{IC}$. More specifically, if shrinkage fitting power or force were wholly lost due to the opening deformation of a crack, loosening would develop in the fitted member and the operation of the rotor would become dangerous.

Figure 2A:
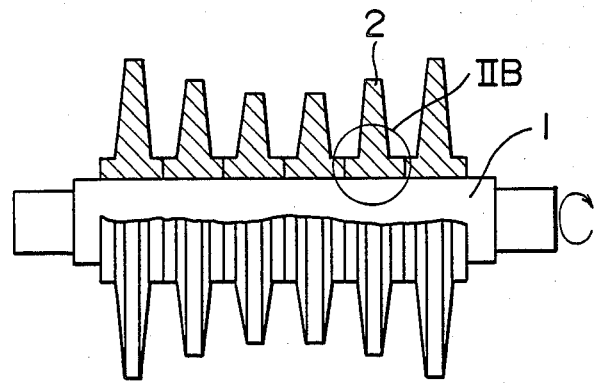
FIG. 2A is a partially broken away, schematic view of the rotor in which a crack is formed.
Figure 2B:
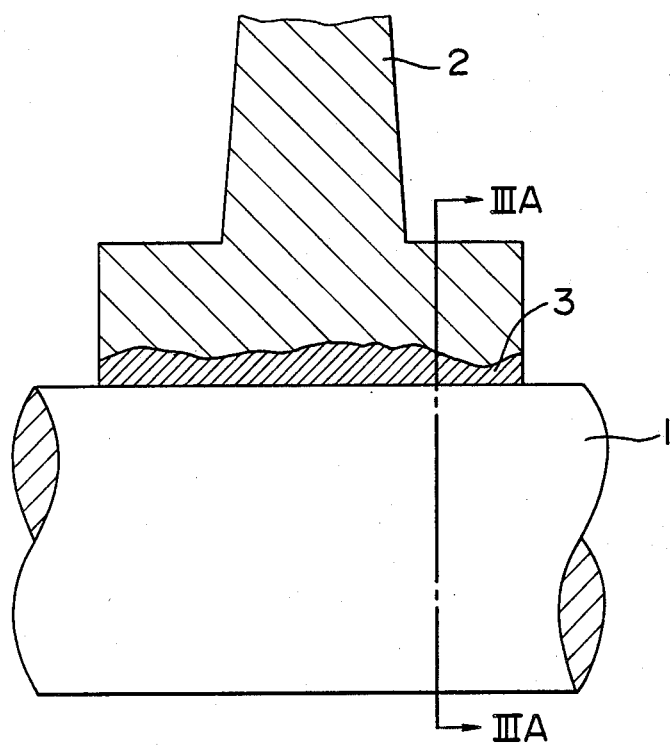
FIG. 2B is a view, on an enlarged scale, of the portion encircled by IIB in FIG. 2A.

FIG. 2A is a schematic view of a rotor of a shrinkage fitted type including a rotary shaft 1 and fitted members 2 shrinkage fitted over the rotary shaft 1. The portion IIB of the rotor shown in FIG. 2A is shown on an enlarged scale in FIG. 2B. As shown, when an axially oriented crack 3 is formed due to some cause in the fitting portion of the fitted member 2 which is shrinkage fitted over the rotary shaft 1, the crack 3 is subjected by the shrinkage fitting force and centrifugal forces to opening deformation as shown in FIG. 1.

Figure 3A:
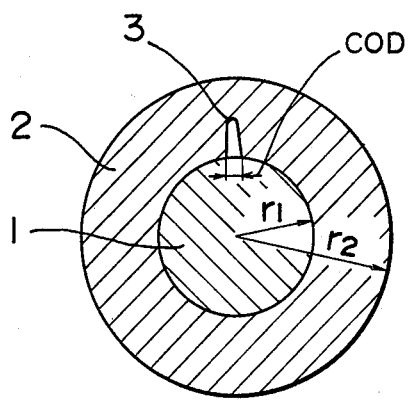
FIG. 3A is a cross-sectional view taken along the line IIIA—IIIA in FIG. 2B.

Referring to FIG. 3A, the shrinkage fitting force F can be expressed by the following equation:

$$F = \frac{E\delta}{2\gamma_1}\left[1 - \left(\frac{r_1}{r_2}\right)^2\right] \quad (1)$$

where $r_1$ denotes the external radius of the rotary shaft 1 and the internal radius of the fitted member 2, $r_2$ denotes the external radius of the fitted member 2, E is the modulus of elasticity and $\delta$ is one-half the interference (or the external radius of the rotary shaft 1 before shrinkage fitting minus the internal radius of the fitted member).

Assuming that the crack 3 is formed at the fitting portion of the fitted member 2 and the crack 3 has an opening displacement COD and that the interference during rotation is $\delta_1$ when there is no crack. Then the interference $\delta$ can be expressed as follows:

$$\delta = \delta_1 - \frac{COD}{2\pi} \quad (2)$$

By substituting equation (2) into equation (1) and arranging the equation (1) by using shrinkage fitting $F_i$ during rotation when there is no crack, the following relationship holds:

$$F = F_i - \frac{E \cdot COD}{2\gamma}\left[1 - \left(\frac{r_1}{r_2}\right)^2\right] \quad (3)$$

Figure 3B:
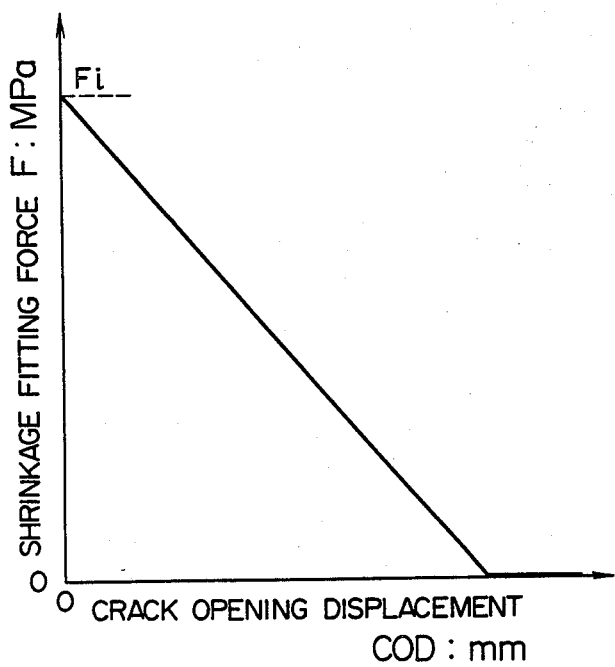
FIG. 3B is a graphical representation of the relationship between the crack opening displacement (COD) and shrinkage fitting force (F)

Thus, the relationship between the opening displacement COD of the crack 3 and the shrinkage fitting force F is as shown in FIG. 3B. In FIG. 3B, it will be seen that the opening deformation of the crack 3 reduces the shrinkage fitting force F, and that the shrinkage fitting force F is totally lost when the opening displacement COD of the crack 3 reaches a certain level. When there is no shrinkage fitting force F, play appears between the rotary shaft 1 and fitted member 2, giving rise to a very dangerous condition. That is, the fitted member 2 might be brought into contact with the stator and casing.

For reasons stated hereinabove, a reduction in shrinkage fitting force F due to the opening deformation of the crack 3 is used in the method of assessing the safety of the rotor according to the invention. The embodiment shown and described hereinabove offers the advantages that a reduction in shrinkage fitting force due to the opening deformation of a crack can be determined quantitatively, and that an accident which might otherwise be caused to occur by the loosening of the fitted member due to the absence of shrinkage fitting force can be avoided.

Figure 6:
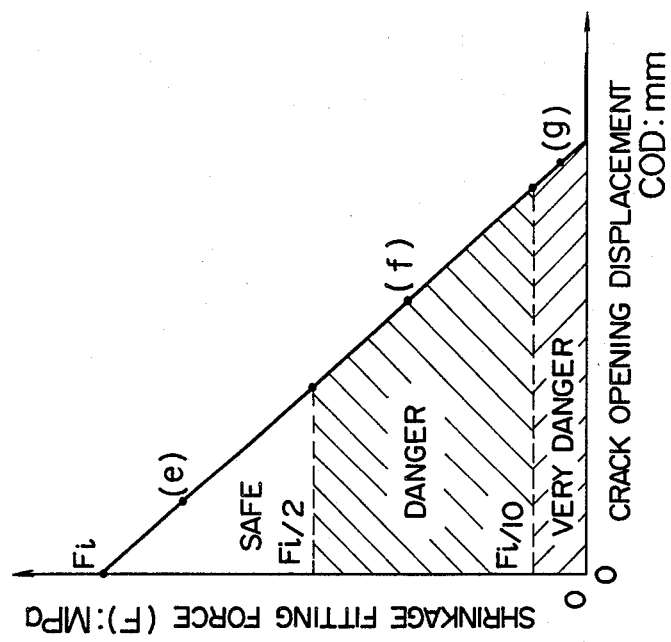
FIG. 6 is a graphical representation in explanation of the standards by which to assess the safety of the rotor based on a reduction in shrinkage fitting force.
Figure 5:
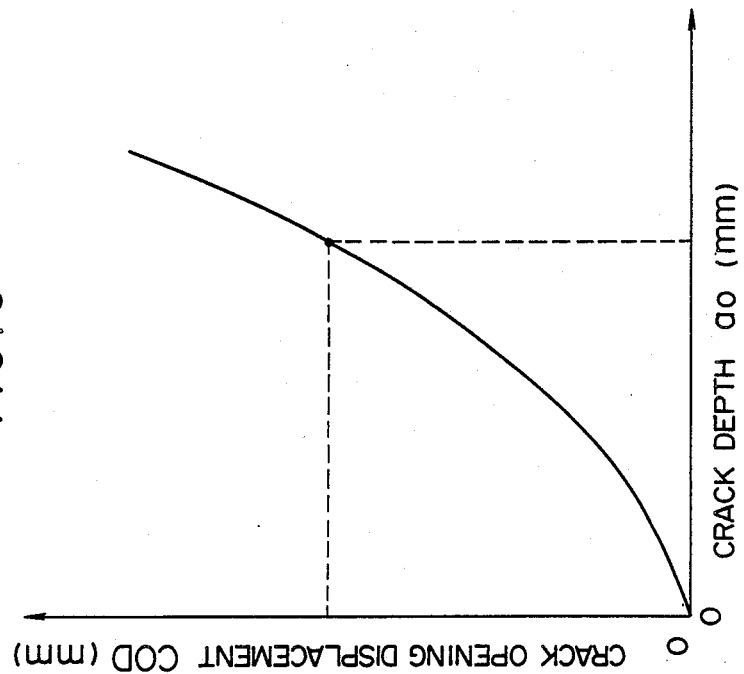
FIG. 5 is a graphical representation of the relationship between the crack depth ($a_o$) and crack opening displacement (COD)

Process steps followed in the embodiment shown and described hereinabove will be described by referring to a flow chart shown in FIG. 4. FIG. 5 shows the relationship between the depth of a crack and the opening displacement of the crack, and FIG. 6 shows the standards of safety assessment. In this embodiment the depth of a crack formed in a rotor of a shrinkage fitted type is measured by following the steps shown in FIG. 4. Then, the crack opening displacement COD is calculated based on the relationship between the crack depth $a_o$ and the crack opening displacement COD shown in FIG. 5. The relationship shown in FIG. 5 may vary depending on the type, material and size of the rotor, so that it is necessary to previously determine the relationship for each case. To determine the relationship, deformation analysis carried out by a finite element method using a computer or other method may be used. When it is possible to measure the crack opening displacement COD directly, the value obtained by directly measuring the crack opening may be used. Thereafter, shrinkage fitting force F is calculated based on the relationship between the crack opening displacement COD and the shrinkage fitting force F shown in FIG. 3B. When it is possible to measure the shrinkage fitting force F directly (by the measurement of the use of the strain gauge, for example), the value of the shrinkage fitting force F obtained by directly measuring the same may be used.

By using the shrinkage fitting force F calculated or measured as described hereinabove, the safety of the rotor is assessed in accordance with the graph shown in FIG. 6 as being safe (e), dangerous (f) or very dangerous (g). Here, a reduction in shrinkage fitting force F, that may involve no risks even if a rotor of shrinkage fitted type is operated while leaving a crack unattended, is set at ½ the value of initial shrinkage fitting force $F_i$ of the rotor rotating with no crack formation. The safety standard ($F_1/2$) may, of course, vary depending on the type of the rotor, and the safety standards for coping with a reduction in shrinkage fitting force may be set in the range between ⅔ and ⅓ the initial shrinkage fitting force $F_i$ of different types. The range of shrinkage fitting force levels which is considered so low that further operation of the rotor would be very dangerous and its operation should be stopped at once is set at a level below 1/10 the initial shrinkage fitting force $F_i$. In setting this standard, some reserve is provided because the operation would be endangered if shrinkage fitting force were completely lost, and because any error that might occur in the measured value of the crack depth and in the calculated value of the shrinkage fitting force is taken into consideration. When the rotor is assessed to be in intermediate zone between the safe and very dangerous zones, preparation should be made for repairing the rotor or replacing the old fitted member with a new one. At this time, operation may be continued by taking necessary steps, such as reducing the rotational speed, although the type of the rotor and the degree of the loss of shrinkage fitting force would have to be taken into consideration. When the rotor is assessed to be so dangerous that no further operation is warranted, measures are taken to replace or repair the fitted member. However, when the rotor is assessed to be fit for further continuation of the operation, the length of service life that the rotor would have is usually further predicted. This step is taken because, if a crack formed in the rotor is due to stress corrosion cracking or fatigue, crack extension would take place with lapse of the operation time and an increase in the crack depth would result in an increase in the opening deformation of the crack. Thus, crack extension, opening deformation of the crack and shrinkage fitting force which would prevail after lapse of a predetermined operation time are predicted as shown in FIG. 4, and assessment of the safety of operation of the rotor in the future is carried out through steps 100, 200 and 300 respectively.

The embodiment shown and described hereinabove offers the advantages that the safety of a rotor of a shrinkage fitted type can be assessed objectively and plans for its operation can be made readily based on the result obtained. Furthermore, by predicting its probable further service life, the invention enables assessment of the safety of operation in the future to be made. Thus, based on the results obtained, programs for repairing the rotor or replacing it or its component with a new one can be readily made and the time for carrying out the next following periodic inspection can be definitely set.

Figure 7:
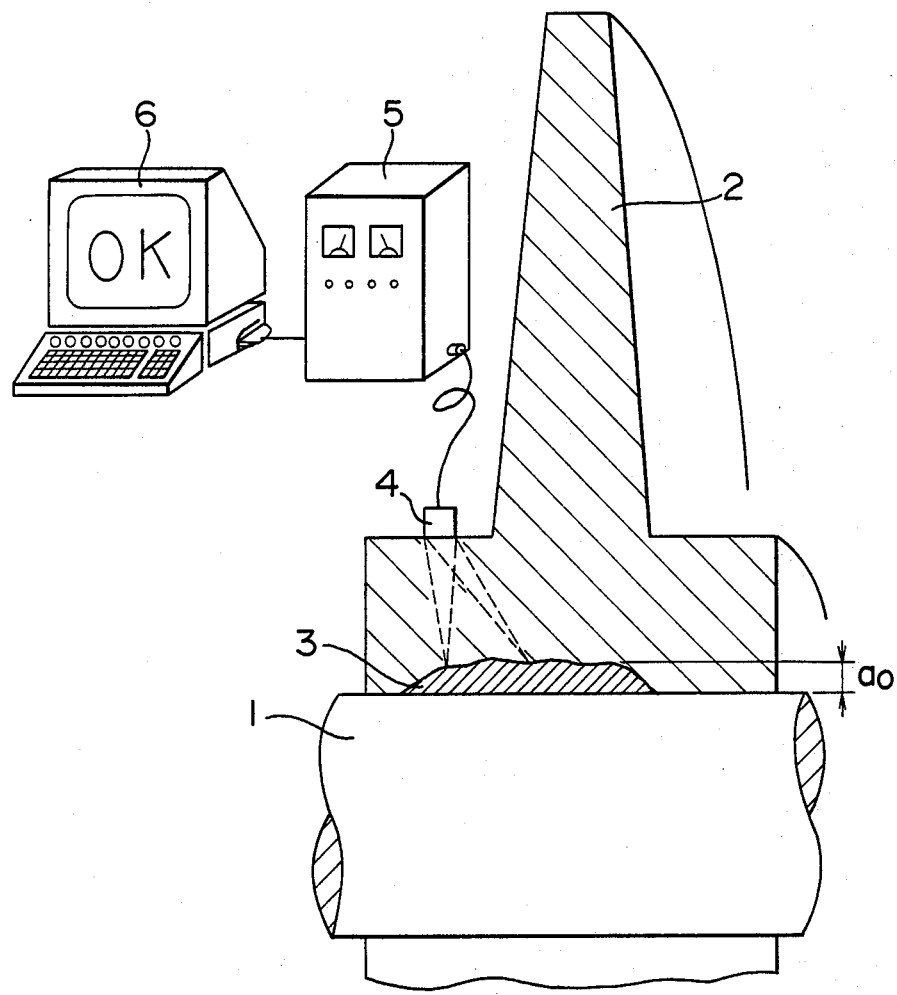
FIG. 7 is a view in explanation of one embodiment of the system for assessing the safety of the rotor.

FIG. 7 shows one embodiment of the system for assessing the safety of operation of a fitted member in conformity with the invention. When a crack 3 is formed in the fitted member 2 shrink fitted over the rotary shaft 1, an ultrasonic flaw detecting device comprising a flaw detector 4 and a measuring and processing unit 5 is used to perform a nondestructive inspection to determine the configuration (depth $a_o$) of the crack 3. When there are a plurality of cracks 3 in the fitted member 2, the depth $a_o$ of each one of the cracks 3 or only a single typical one of the cracks 3 may be measured. The measurement of the depth $a_o$ of the crack 3 is inputted to a micro-computer 6 which calculates the crack opening displacement COD and the shrinkage fitting force F based on the relationships shown in FIG. 5 and FIG. 3, respectively. The calculated values COD and F are processed so that assessment of the safety of operation of the rotor is made based on the standards by which the safety of operation should be assessed as shown in FIG. 6. The data are processed by the microcomputer 6 by following the process steps shown in the flow chart in FIG. 4. The use of the system shown in FIG. 7 assures that loosening of the rotor, which might otherwise be caused by a reduction in shrinkage fitting force F, can be avoided, because assessment of the safety of operation of the rotor can be made objectively before fracture commences.

What is claimed is:

1. (Amended) A method of assessing the safety of a rotor of a shrinkage fitted type including a rotary shaft and a fitted member shrinkage over said rotary shaft, said method comprising the steps of:

measuring a depth of a crack formed in a fitting portion of said fitted member;

determining an opening displacement of the crack by an elastic-plastic fracture method;

calculating a reduction in shrinkage fitting force based on the determined opening displacement; and comparing the determined opening displacement and the reduced shrinkage fitting force of said fitted member with a predetermined safety-assessment standard to thereby assess the safety of the rotor.

2. A method as claimed in claim 1, wherein an allowable reduction in shrinkage fitting force which permits further operation of the rotor having a crack formed therein is set at ½ the initial shrinkage fitting force determined during operation without crack formation.

3. A method as claimed in claim 1, wherein an allowable reduction in shrinkage fitting force is set in the range between ⅓ and ⅔ the initial shrinkage fitting force.

4. A method as claimed in claim 1, wherein a critical reduced shrinkage fitting force indicating instantaneous shutdown of the rotor is set as less than 1/10 the initial shrinkage fitting force.

5. A method of assessing a safety of a rotor of a shrinkage fitted type including a rotor shaft and a fitted member shrinkage fitted over said rotary shaft, said method comprising the steps of:

measuring an opening displacement of a crack formed in a fitting portion of said fitted member;

calculating a reduction in shrinkage fitting force of said fitted member based on the measured crack opening displacement; and comparing the reduced shrinkage fitting force of said fitted member with a predetermined safety-assessment standard to thereby assess the safety of the rotor.

6. (Amended) A method of assessing the safety of a rotor of a shrinkage fitted type including a rotary shaft and a fitted member shrinkage fitted over said rotary shaft, said method comprising the steps of:
  measuring a reduction in shrinkage fitting force; and
  comparing the reduced shrinkage fitting force of said fitted member with a predetermined safety-assessment standard to assess the safety of said rotor.

7. A system for assessing the safety of a rotor of a shrinkage fitted type including a rotary shaft and a fitted member shrinkage fitted over said rotary shaft, said system comprising:
  an ultrasonic flaw detector for detecting a first signal representative of a depth of a crack in said fitted member to generate a second signal;
  a first operating means for determining the depth of the crack based on the second signal from the ultrasonic flaw detector;
  a second operating means for determining an opening displacement of the crack based on the determined crack depth by an elastic-plastic fracture method;
  a third operating means for determining a reduced fitting force of said fitted member on the basis of the determined crack opening displacement; and
  a further means for comparing the determined crack opening displacement and the determined reduced fitting force with a pre-determined safety assessment standard to thereby assess the safety of said rotor.

* * * * *